(12) United States Patent
Kaneko et al.

(10) Patent No.: US 6,521,656 B1
(45) Date of Patent: Feb. 18, 2003

(54) REMEDIES FOR MALE STERILITY

(75) Inventors: Satoru Kaneko, Ichikawa (JP); Kazuhiko Nomura, Ibaraki (JP); Yutaka Kohno, Ibaraki (JP); Hiroshi Kodama, Tsukuba (JP); Tokuaki Kajiho, Kobe (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/701,385

(22) PCT Filed: May 28, 1999

(86) PCT No.: PCT/JP99/02811

§ 371 (c)(1), (2), (4) Date: Jan. 4, 2001

(87) PCT Pub. No.: WO99/62553

PCT Pub. Date: Dec. 9, 1999

(30) Foreign Application Priority Data

Jun. 1, 1998 (JP) ............................. 10-151224
Nov. 9, 1998 (JP) ............................. 10-317795

(51) Int. Cl.$^7$ ................... A61K 31/415; A61K 31/495; A61K 31/50; A61K 31/42

(52) U.S. Cl. ................... 514/406; 514/403; 514/405; 514/252.01; 514/252.05; 514/252.06; 514/379

(58) Field of Search ............... 514/252.01, 252.05, 514/252.06, 379, 406, 405, 403

(56) References Cited

FOREIGN PATENT DOCUMENTS

| WO | WO-95/11681 A1 | * | 5/1995 | ........... A61K/31/52 |
|---|---|---|---|---|
| WO | WO-95/18128 A1 | * | 7/1995 | ......... C07D/471/04 |

OTHER PUBLICATIONS

Uehara et al., Am. J. Hypertens. (1995), 8(12, pt 1), 1189–99.*

Kaneko et al., Dokkyo Igakkai Zasshi, 1995 10(2), 235–44.*

Zarifian A. A., Anna Journal, (Dec. 1992) 19 (6) 527–32.*

* cited by examiner

Primary Examiner—Russell Travers
Assistant Examiner—S. Jiang

(57) ABSTRACT

Efficacious remedies for male sterility which are in the form of preparations containing as the active ingredient an adenosine $A_1$ antagonist.

14 Claims, No Drawings

REMEDIES FOR MALE STERILITY

This application is a filing under 35 U.S.C. 371 of PCTJP99/02811, filed May 28, 1999.

TECHNICAL FIELD

The present invention relates to a therapeutic agent for male sterility which comprises an adenosine $A_1$ antagonist or a salt thereof as an active ingredient and so is useful in the pharmaceutical field.

BACKGROUND ART

The infertile male population has recently been on the steady increase and, alongside endocrine disruptors in environment inclusive of dioxins, the so-called male sterility is a matter of serious concern to the society at large.

However, no satisfactory remedy has been established for the therapy of this disease as yet and the assisted reproductive technology such as intracytoplasmic (intraoosomal) sperm injection (ICSI) is an exclusive choice available today. ICSI is a laudably effective fertilizing method but is defective in terms of safety in that the genetic check of the sperm cannot be made. Furthermore, because the selection of fertile sperm is entrusted to the human hand, the method has ethically a negative aspect and, in addition, since the cost of the procedure is exorbitant and not covered by an insurance, many patients have to abandon the idea to receive the treatment.

Therefore, there is a keen demand from the medical scene for a fertilizing technology which would be less costly than ICSI and more natural in that the sperm would be encouraged to enter the ova by its own efforts.

The acrosomal reaction is indispensable to the penetration of sperm through the pellucid zone of the ovum and it is considered to be very efficacious to promote the induction of sperm acrosomal reaction of sperm for the therapy of male sterility.

It is generally considered that the induction of sperm acrosomal reaction in infertile men can be promoted by inhibiting the sperm phosphodiesterase and, aiming at this inhibition, such drugs as caffeine and pentoxiphylline have been used on an empirical basis.

However, the promotion of induction of sperm acrosomal reaction with such drugs has not been fruitful enough.

In the field of therapy for male sterility today, there exists a demand for an effective acrosomal reaction induction promoter and the present invention has for its object to solve the above problem.

DISCLOSURE OF INVENTION

The present inventor obtained a novel finding quite dissimilar to the earlier notion, namely "the induction of acrosomal reaction can be promoted by inhibiting the binding of adenosine to the adenosine $A_1$ receptor of the sperm", has accomplished the present invention. The present invention, therefore, provides a therapeutic composition comprising an adenosine $A_1$ receptor antagonist or a salt thereof as an active ingredient to thereby solve the above-mentioned problem.

To demonstrate that the induction of acrosomal reaction in infertile men can be promoted by inhibiting the binding of adenosine to the adenosine $A_1$ receptor of the sperm, the influence of adenosine $A_1$ antagonists on the human sperm acrosomal reaction was investigated using the following test compounds which are well-known specific adenosine $A_1$ antagonists.

Test Compounds (A) 3-[2-(3-Carboxypropyl)-3-oxo-2,3-dihydropyridazin-6-yl]-2-phenylpyrazolo[1,5-a]pyridine (B) (2R)-1-[3-(2-Phenylpyrazolo[1,5-a]pyridin-3-yl)acryloyl]-2-(carboxymethyl)piperidine (trans-isomer)

(C) 3-[2-(2-Carboxymethyl-1-cyclohexenyl)-3-oxo-2,3-dihydropyridazin-6-yl]-2-phenylpyrazolo[1,5-a]pyridine Test for Evaluation of the Promoting Effect on the Induction of Sperm Acrosomal Reaction 1. Method Percoll for sperm washing was isotonized and adjusted to 90% with 20 mM Hepes buffered Hanks solution (pH 7.4; supplemented with 1.0 mg/ml BSA). The ejaculated human seminal fluid was allowed to liquefy at room temperature, diluted 2-fold with Hanks solution, and layered on 6.0 ml Percoll. In the Percoll layer, a glass capillary had been inserted in advance. The system was centrifuged at 1000×g for 30 minutes to precipitate motile sperm. The precipitated sperm was aspirated through the capillary and recovered. The sperm was resuspended in Hanks solution at a final concentration of about $50 \times 10^6$/ml and cultured at 37° C.

The human sperm acrosomal reaction was monitored by a fluorescence staining technique using FITC-concanavalin A.

As the acrosomal cap splits off on acrosomal reaction, the membrane protein rich in the high-mannose sugar chain on the acrosomal tunica intima becomes exposed. Therefore, the sperm showing a yellow fluorescence in the anterior half of the head was regarded as acrosomal reaction-induced sperm.

Compound A was added to the sperm suspension at a final concentration of $10^{-6}$ or $10^{-7}$ M. Observation was made in the group supplemented with 1 I.U./ml of adenosine deaminase and the non-enzyme-addition group.

Compounds B and C were respectively added to the sperm suspension at a final concentration of $10^{-7}$ M. Observation was made in the groups supplemented with 1 I.U./ml of adenosine deaminase.

2. Results

The test results are shown in the following tables. Each figure denotes the acrosomal reaction induction rate (%) (the mean±S.E. of 3 observations in Table 1; the mean±S.E. of 5 observations in Tables 2 and 3). In Table 1, the figure in the top row represents the result obtained in the absence of adenosine deaminase and the figures in the bottom row represent the results in the presence of adenosine deaminase.

TABLE 1

| Incubation | Compound A, concentration (M) | | |
| --- | --- | --- | --- |
| time | 0 | $10^{-6}$ | $10^{-7}$ |
| 0 | 6.54 ± 1.87 | — | — |
| 3 | 27.1 ± 2.35 | 43.7 ± 2.77 | 47.1 ± 2.37 |
|   | 32.7 ± 2.45 | 63.6 ± 1.84 | 64.1 ± 1.73 |

TABLE 2

| Incubation time | Compound B, concentration (M) | |
|---|---|---|
| | 0 | $10^{-7}$ |
| 3 | 30.98 ± 1.17 | 41.26 ± 2.18 |

TABLE 3

| Incubation time | Compound C, concentration (M) | |
|---|---|---|
| | 0 | $10^{-7}$ |
| 3 | 34.20 ± 2.93 | 48.86 ± 2.57 |

The finding that the induction of acrosomal reaction was promoted in the presence of adenosine deaminase suggests that the induction of acrosomal reaction is inhibited in the presence of adenosine. Furthermore, the finding that the induction of acrosomal reaction was promoted by Compounds A, B and C, which are specific adenosine $A_1$ antagonists, suggests that the induction of acrosomal reaction is inhibited by the binding of adenosine to the adenosine $A_1$ receptor.

It has, thus, been proven that adenosine $A_1$ antagonists promote the induction of acrosomal reaction.

The present invention is carried into practice by submitting an adenosine $A_1$ antagonist or a salt thereof, either as it is or in the form of a pharmaceutical composition containing an adenosine $A_1$ antagonist or a salt thereof as an active ingredient, to a patient with male sterility.

The term "adenosine $A_1$ antagonist" as used in this specification means a substance that opposes the action of adenosine on adenosine $A_1$ receptors and includes all substances falling within the category of "adenosine $A_1$ antagonist" as established in the art. A large number of compounds are already known as adenosine $A_1$ antagonists and. even novel compounds that is regarded as adenosine $A_1$ antagonists should also be included in the category of adenosine $A_1$ antagonists in the context of the present invention.

The existence as well as the intensity of action of "adenosine $A_1$ antagonist" can be evaluated typically by the following method. The intensity of adenosine $A_1$ antagonist action as referred to in the claims also means a quantity found by the following evaluation method.

Test for Adenosine $A_1$ Antagonist Action
(1) Preparation of a Rat Brain Homogenate The rat brain homogenate is used in the adenosine $A_1$ receptor binding assay. The brains isolated from male SD rats weighing about 200~300 g are homogenized in 20 parts (w/v) of 50 mM Tris-HCl buffer (pH 7.4, 25° C.) using Polytron homogenizer (Kinematica GmbH). The homogenate is centrifuged (4° C.) at 41000×g for 30 minutes. The resulting pellet is resuspended in 20 parts of buffer solution (50 mM, pH 7.4). To this is added adenosine deaminase (2 I.U./ml) and the mixture is incubated at 37° C. for 30 minutes to remove the endogenous adenosine. This brain homogenate is recentrifuged and the resulting pellet is stored frozen at −70° C. until used in the binding assay.

(2) The Receptor Binding Assay using [$^3$H]-N$^6$-Cyclohexyladenosine ($^3$H-CHA) as a Radioligand The assay is performed in a system containing 1 nM $^3$H-CHA with a specific activity of 25 Ci/mmol and giving a final volume of 1 ml. Non-specific binding is determined in the presence of CHA (10 μM).

The reaction is started by adding the brain homogenate mentioned above at a final protein concentration of 200~300 μg/ml and the reaction mixture is incubated at 23° C. for 3hours. After this incubation, the bound radioactivity is isolated by filtration under vacuum through a Whatman GF/B glass fiber filter and the unbound radioactivity is washed off with 5 ml of ice-cooled buffer solution twice. The filter for each sample is placed in a glass vial, to which Aquasol II (manufactured by NEN Research Products) (10 ml) is added. After at least 12 hours of standing, the radioactivity is measured by the standard liquid scintillation spectroscopy.

In carrying the present invention into practice, it is advisable to use a specific adenosine $A_1$ antagonist having sufficiently high adenosine $A_1$ antagonist activity. For example, a compound giving an $IC_{50}$ value of not more than 100 μM, preferably not more than 50 μM, more preferably not more than 10 μM, particularly not more than 1 μM, in the above assay can be used with advantage. (Any one skilled in the art should interpret the above values with experimental errors and other variables taken into consideration). Thus, these values should be considered to be rules of thumb and rather one skilled in the art can judiciously select an adenosine $A_1$ antagonist suitable for the present invention by carrying out the above "Test for evaluation of the promoting effect on the induction of acrosomal reaction" and "Test for adenosine $A_1$ antagonist action".

In the above sense, a compound additionally possessed of a pharmacologic action other than adenosine $A_1$ antagonist action can likewise be used.

Structurally, pyrazolopyridine compounds of the following general formula (I) and their salts can be mentioned as typical examples of the adenosine $A_1$ antagonist.

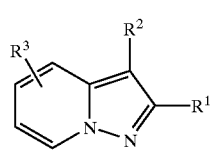

(I)

[wherein $R^1$ is a lower alkyl, aryl which may have one or more suitable substituent(s), or a heterocyclic group, $R^2$ is a group of the formula:

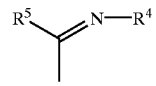

(wherein $R^4$ is protected amino or hydroxy and $R^5$ is hydrogen or lower alkyl);

cyano;

a group of the formula:

(wherein $R^6$ is an acyl group and A is a lower aliphatic hydrocarbon group which may have one or more suitable substituent(s));

amidated carboxy;

unsaturated heterocyclic group which may have one or more suitable substituent(s);

amino; or protected amino, and $R^3$ is hydrogen, lower alkyl, lower alkoxy, or halogen].

As the above pyrazolopyridine compound (I), there can be mentioned the known compounds described in, inter alia, Japanese laid-open (Kokai Tokkyo Koho) No. S64-45385, H2-243689, H4-253978, and H5-112566, and WO95/18128.

Suitable salts of the pyrazolopyridine compound (I) are pharamceutically acceptable salts of the conventional kinds, for example metal salts such as alkali metal salts, (e.g. sodium salt, potassium salt, etc., and alkaline earth metal salts, e.g. calcium salt, magnesium salt, etc.), ammonium salts, organic base salts, such as trimethylamine salt, triethylamine salt, pyridine salt, picoline salt, dicyclohexylamine salt, N,N'-dibenzylethylenediamine salt, etc., organic acid salts, such as acetate, trifluoroacetate, maleate, tartrate, fumarate, methanesulfonate, benzenesulfonate, formate, toluenesulfonate, etc., inorganic acid salts, such as hydrochloride, hydrobromide, hydroiodide, sulfate, phosphate, etc., and salts with amino acids such as arginine, aspartic acid, glutamic acid and so on.

Suitable examples and particulars of various terms defining the above pyrazolopyridine compound (I) are explained hereinbelow in detail.

The term "lower" is intended to mean 1 to 6 carbon atom(s), unless otherwise indicated.

The term "higher" is intended to mean 7 to 20 carbon atoms, unless otherwise indicated.

Suitable "lower aliphatic hydrocarbon group" may include the following lower alkyl, lower alkenyl and lower alkynyl groups.

Suitable "lower alkyl" may include straight or branched ones such as methyl, ethyl, propyl, isopropyl, butyl, tert-butyl, pentyl, hexyl or the like, and among these, the preferred one maybe ($C_1$–$C_4$)alkyl and the more preferred one may be methyl, ethyl, propyl and isopropyl.

Suitable "lower alkenyl" may include straight or branched ones such as vinyl, 1-methylvinyl, 2-methylvinyl, 1-propenyl, 2-propenyl, 1-butenyl, 2-methyl-1-propenyl, 1,3-butadienyl, 1-pentenyl, 4-pentenyl, 1-hexenyl, 1,4-hexadienyl, 5-hexenyl or the like, and among these, the preferred one may be ($C_2$–$C_4$)alkenyl and the more preferred one may be vinyl, 1-methylvinyl, 2-methylvinyl and 1,3-butadienyl.

Suitable "lower alkynyl" may include straight or branched ones such as ethynyl, 1-propynyl, 1-methylethynyl, 2-butynyl, 2-methyl-3-butynyl, 2-pentynyl, 1-hexynyl or the like, and among these, the preferred one may be ($C_2$–$C_4$) alkynyl and the more preferred one may be ethynyl.

The "lower aliphatic hydrocarbon group" mentioned above may have one or more, preferably 1 to 3, suitable substituent(s) such as halogen, (e.g. chloro, bromo, fluoro and iodo).

Suitable "protected amino group" may include amino substituted with the conventional amino-protective groups, such as lower alkylamino, (e.g. methylamino, ethylamino, propylamino, butylamino, tert-butylamino, pentylamino, hexylamino, etc.), di(lower)alkylamino, (e.g. dimethylamino, diethylamino, N-ethylpropylamino, dibutylamino, N-(tert-butyl)pentylamino, dihexylamino, etc.), and the acylamino groups mentioned below.

Suitable "acylamino" may include ureido; lower alkanoylamino, (e.g. formylamino, acetylamino, propionylamino, butyrylamino, isobutyrylamino, pivaloylamino, hexanoylamino, etc.); lower alkoxycarbonylamino, (e.g. methoxycarbonylamino, ethoxycarbonylamino, propoxycarbonylamino, tert-butoxycarbonylamino, pentyloxycarbonylamino, hexyloxycarbonylamino, etc.); lower alkoxycarbonyl (lower)alkanoylamino, (e.g. methoxycarbonylacetylamino, ethoxycarbonylacetylamino, 2-(propoxycarbonyl)-propionylamino, 4-(tert-butoxycarbonyl)butyrylamino, 2-(butoxycarbonylmethyl)propionylamino, 2-methyl-2-(pentyloxycarbonylmethyl)-propionylamino, 6-hexyloxycarbonylhexanoylamino, etc.); and lower alkanesulfonylamino, (e.g. methanesulfonylamino, ethanesulfonylamino, propanesulfonylamino, butanesulfonyl amino, tert-butanesulfonylamino, pentanesulfonylamino, hexanesulfonylamino, etc).

The "lower alkanoylamino" mentioned above may have suitable substituent(s) such as di(lower)alkylamino groups, (e.g. dimethylamino, N-methyl-N-ethylamino, dipropylamino, di-tert-butylamino, N-pentyl-N-hexylamino, etc.); and cyclic amino groups which may have suitable substituents, (e.g. piperidino, etc.). Suitable examples of the said "lower alkanoylamino groups having suitable substituent(s)" may include lower alkanoylamino having di(lower)alkylamino, such as dimethylaminocarbonylamino, 2-dimethylaminoacetylamino, 2-(N-methyl-N-ethylamino) acetylamino, 2-dimethylaminopropionylamino, 3-dipropylaminobutyrylamino, 2-(di-tert-butylamino)-2-methylpropionylamino, 2-dimethylaminomethyl-2-methylpropionylamino, 6-(N-pentyl-N-hexylamino) hexanoylamino or the like; and lower alkanoylamino having cyclic amino groups optionally having lower alkyl, such as piperidinocarbonylamino, 2-piperidinoacetylamino, 2-(2-methylpiperidino)acetylamino, 2-(2-ethylpiperidino) acetylamino, 2-piperidinopropionylamino, 3-(2-ethylpiperidino)butyrylamino, 2-(4-ethylpiperidino)-2-methylpropionylamino, 2-piperidinomethyl-2-methylpropionylamino, 6-(3-propylpiperidino) hexanoylamino or the like.

In aforesaid "acylamino", the preferred one may be ureido, ($C_1$–$C_4$)alkanoylamino, ($C_1$–$C_4$)alkoxycarbonyl ($C_1$–$C_4$)alkanoylamino, di($C_1$–$C_4$)alkylamino($C_1$–$C_4$) alkanoylamino, ($C_1$–$C_4$) alkylpiperidino($C_1$–$C_4$) alkanoylamino, ($C_1$–$C_4$) alkoxycarbonylamino, ($C_1$–$C_4$) alkanesulfonylamino, ($C_1$–$C_4$)alkylamino and di($C_1$–$C_4$) alkylamino, in which the more preferred one may be ureido, acetylamino, 2-(ethoxycarbonyl)acetylamino, 2-dimethylaminoacetylamino, 2-(2-ethylpiperidino) acetylamino, methoxycarbonylamino, methanesulfonylamino, methylamino and dimethylamino.

Suitable "acyl" may include lower alkanoyl such as formyl, acetyl, propionyl, butyryl, isobutyryl, pivaloyl, hexanoyl or the like; carboxy; and protected carboxy, and so on.

Suitable example of aforesaid "protected carboxy" may include esterified carboxy, the suitable example of which is lower alkoxycarbonyl, (e.g. methoxycarbonyl, ethoxycarbonyl, propoxycarbonyl, butoxycarbonyl, tert-butoxycarbonyl, pentyloxycarbonyl, hexyloxycarbonyl, etc.), which may have nitrogen-containing heterocyclic group; and amidated carboxy, the suitable examples of which are
N-(lower)alkylcarbamoyl such as N-methylcarbamoyl, N-ethylcarbamoyl, N-isopropylcarbamoyl, N-butylcarbamoyl, N-pentylcarbamoyl, N-hexylcarbamoyl or the like;
N-(higher)alkylcarbamoyl such as N-heptylcarbamoyl, N-(2-methylheptyl)carbamoyl, N-nonylcarbamoyl, N-decanylcarbamoyl, N-tricyclo[$3.3.1.1^{3,7}$] decanylcarbamoyl, N-undecanylcarbamoyl, N-(bicyclo [4.3.2]undecanyl)carbamoyl, N-dodecanylcarbamoyl, N-tridecanylcarbamoyl, N-tetradecanylcarbamoyl, N-pentadecanylcarbamoyl, N-hexadecanylcarbamoyl, N-heptadecanylcarbamoyl, N-octadecanylcarbamoyl, N-nonadecanylcarbamoyl, N-icosanylcarbamoyl or the like;

N,N-di(lower)alkylcarbamoyl such as N,N-dimethylcarbamoyl, N,N-diethylcarbamoyl, N-methyl-N-ethylcarbamoyl, N,N-dipropylcarbamoyl, N,N-di(tert-butyl)carbamoyl, N-pentyl-N-hexylcarbamoyl or the like;

N-(lower)alkyl-N-ar(lower)alkylcarbamoyl such as N-methyl-N-benzylcarbamoyl or the like; a group of the formula:

(wherein $R_N$ is nitrogen-containing heterocyclic group optionally having one or more suitable substituent(s) this nitrogen-containing heterocyclic group $R_N$ may contain another hetero atom(s) such as N, O and/or S in its ring).

Suitable "nitrogen-containing heterocyclic group" may include saturated or unsaturated, monocyclic or polycyclic heterocyclic group such as unsaturated 3 to 8-membered (more preferably, 5 to 7-membered) heteromonocyclic group containing 1 to 4 nitrogen atom(s), for example, azepinyl (e.g. 1H-azepinyl, etc.), pyrrolyl, pyrrolinyl, imidazolyl, pyrazolyl, pyridyl and its N-oxide, dihydropyridyl, pyrimidinyl, pyrazinyl, pyridazinyl, triazolyl (e.g. 4H-1,2,4-triazolyl, 1H-1,2,3-triazolyl, 2H-1,2,3-triazolyl, etc.), and tetrazolyl (e.g. 1H-tetrazolyl, 2H-tetrazolyl, etc.);

saturated 3 to 8-membered (more preferably 5 to 7-membered) heteromonocyclic group containing 1 to 4 nitrogen atom(s), for example, perhydroazepinyl (e.g. perhydro-1H-azepinyl, etc.), pyrrolidinyl, imidazolidinyl, piperidino and piperazinyl;

unsaturated condensed heterocyclic group containing 1 to 4 nitrogen atom(s), for example, indolyl, isoindolyl, indolizinyl, benzimidazolyl, quinolyl, isoquinolyl, indazolyl, benzotriazolyl or the like;

saturated condensed heterocyclic group containing 1 to 4 nitrogen atom(s), for example, 7-azabicyclo[2.2.1]heptyl, 3-azabicyclo[3.2.2]nonanyl or the like;

unsaturated 3 to 8-membered (more preferably 5 or 6-membered) heteromonocyclic group containing 1 or 2 oxygen atom(s) and 1 to 3 nitrogen atom(s), for example, oxazolyl, isoxazolyl, and oxadiazolyl (e.g. 1,2,4-oxadiazolyl, 1,3,4-oxadiazolyl, 1,2,5-oxadiazolyl, etc.) or the like;

saturated 3 to 8-membered (more preferably, 5 or 6-membered) heteromonocyclic group containing 1 or 2 oxygen atom(s) and 1 to 3 nitrogen atom(s), for example, morpholinyl, sydnonyl, or the like;

unsaturated fused heterocyclic groups containing 1~2 oxygen atoms and 1~3 nitrogen atoms, such as benzoxazolyl, benzoxadiazolyl, etc.;

unsaturated 3 to 8-membered (more preferably, 5 or 6-membered) heteromonocyclic group containing 1 or 2 sulfur atom(s) and 1 to 3 nitrogen atom(s), for example, thiazolyl, isothiazolyl (e.g. 1,2,3-thiadiazolyl, 1,2,4-thiadiazolyl, 1,3,4-thiadiazolyl, 1,2,5-thiadiazolyl, etc.), dihydrothiazinyl or the like;

saturated 3 to 8-membered (more preferably, 5 or 6-membered) heteromonocyclic group containing 1 or 2 sulfur atom(s) and 1 to 3 nitrogen atom(s), for example, thiazolidinyl or the like;

unsaturated condensed heterocyclic group containing 1 or 2 sulfur atom(s) and 1 to 3 nitrogen atom(s), for example, benzothiazolyl, benzothiadiazolyl or the like.

Among these groups, the preferred one may include saturated 3 to 8-membered heteromonocyclic group containing 1 to 4 nitrogen atom(s), saturated condensed heterocyclic group containing 1 to 4 nitrogen atom(s) and saturated 3 to 8-membered heteromonocyclic group containing 1 or 2 oxygen atom(s) and 1 to 3 nitrogen atom(s).

These nitrogen-containing heterocyclic groups may each have one or more suitable substituent(s) such as lower alkyl as mentioned above; hydroxy(lower)alkyl (e.g. hydroxymethyl, 1-hydroxyethyl, 2-hydroxyethyl, 3-hydroxypropyl, 2-hydroxybutyl, 1-methyl-1-hydroxymethylethyl, 4-hydroxypentyl, 3-hydroxyhexyl, etc.); lower alkoxy(lower)alkyl (e.g. methoxymethyl, 2-methoxyethyl, 1-ethoxyethyl, 3-propoxypropyl, 2-(tert-butoxy)butyl, 5-pentyloxypentyl, 3-hexyloxyhexyl, etc.); acyloxy(lower)alkyl such as lower alkanoyloxy(lower)alkyl (e.g. acetoxymethyl, 1-acetoxyethyl, 2-acetoxyethyl, 2-propionyloxyethyl, 3-propionyloxypropyl, 2-butyryloxybutyl, 4-pivaloyloxypentyl, 6-hexanoyloxyhexyl, etc.); protected carboxy such as said lower alkoxycarbonyloxy; carboxy; acyl(lower)alkyl such as lower alkanoyl(lower)alkyl (e.g. formylmethyl, 1-formylethyl, 2-acetylethyl, 2-formylpropyl, 3-propionylpropyl, 4-formylbutyl, 2-butyrylbutyl, 1-formylmethylethyl, 3-formylpentyl, 1-isobutyrylpentyl, 4-pivaloylpentyl, 2-formylhexyl, 6-hexanoylhexyl, etc.), carboxy(lower)alkyl (e.g. carboxymethyl, 1-carboxyethyl, 2-carboxypropyl, 1-carboxymethylethyl, 4-carboxybutyl, 3-carboxypentyl, 2-carboxyhexyl, etc.), protected carboxy (lower)alkyl [preferably, esterified carboxy(lower)alkyl, more preferably lower alkoxycarbonyl(lower)alkyl such as methoxycarbonylmethyl, 2-methoxycarbonylethyl, 1-ethoxycarbonylethyl, 2-propoxycarbonylpropyl, 1-methoxycarbonylmethylethyl, 4-t-butoxycarbonylbutyl, 3-pentyloxycarbonylpentyl, 2-hexyloxycarbonylhexyl or the like; and amidated carboxy(lower)alkyl, more preferably carbamoyl(lower)alkyl, N-(lower)alkylcarbamoyl(lower)alkyl (e.g. N-ethylcarbamoylmethyl, etc.) and N,N-di(lower)alkylcarbamoyl(lower)alkyl (e.g. N,N-diethylcarbamoylmethyl, etc.)]or the like.

Among said "nitrogen-containing heterocyclic groups" which may have one or more suitable substituent(s)", the preferred one may include piperidino optionally having 1 to 4 suitable substituent(s) selected from a group consisting of $(C_1–C_4)$ alkyl, hydroxy$(C_1–C_4)$alkyl, $(C_1–C_4)$alkoxy $(C_1–C_4)$alkyl, $(C_1–C_4)$ alkoxycarbonyl, carboxy, $(C_1–C_4)$ alkanoyl$(C_{1–C4})$alkyl, carboxy$(C_1–C_4)$alkyl, $(C_1–C_4)$ alkoxycarbonyl$(C_1–C_4)$alkyl, carbamoyl$(C_1–C4)$alkyl, N-$(C_1–C_4)$ alkylcarbamoyl $(C_1–C_4)$ alkyl and N,N-di $(C_1–C_4)$alkylcarbamoyl$(C_1–C_4)$alkyl, such as piperidino, 2-methylpiperidino, 2-ethylpiperidino, 3-ethylpiperidino, 4-ethylpiperidino, 2-propylpiperidino, 4-isopropylpiperidino, 2-butylpiperidino, 3-(tert-butyl)piperidino, 2,2,6,6-tetramethylpiperidino, 2,2-dimethyl-6,6-diethylpipridino, 2-hydroxymethylpiperidino, 3-hydroxymethylpiperidino, 2-(1-hydroxyethyl)piperidino, 2-(2-hydroxyethyl)piperidino, 3-(2-hydroxyethyl) piperidino, 4-(2-hydroxyethyl)piperidino, 2-(3-hydroxypropyl)piperidino, 3-(2-hydroxybutyl)piperidino, 2-(1-methyl-1-hydroxymethylethyl)piperidino, 2-methoxymethylpiperidino, 2-(2-methoxyethyl)piperidino, 2-(1-ethoxyethyl)piperidino, 3-(3-propoxypropyl) piperidino, 4-{2-(tert-butoxy)butyl}-piperidino, 2-acetoxymethylpiperidino, 3-(1-acetoxyethyl)piperidino, 2-(2-acetoxyethyl)piperidino, 3-(2-propionyloxyethyl) piperidino, 4-(3-propionyloxypropyl)piperidino, 2-(2-butyryloxybutyl)piperidino, 2-methoxycarbonylpiperidino, 2-ethoxycarbonylpiperidino, 2-propoxycarbonylpiperidino, 3-butoxycarbonylpiperidino, 4-(tert-butoxycarbonyl)

piperidino, 2-carboxypiperidino, 3-carboxypiperidino, 4-carboxypiperidino, 2-(2-hydroxyethyl)-3-methylpiperidino, 2-(2-hydroxyethyl)-4-carboxypiperidino, 2-formylmethylpiperidino, 2-(1-formylethyl)piperidino, 3-(2-acetylethyl)piperidino, 4-(2-formylpropyl)piperidino, 2-(3-propionylpropyl)piperidino, 2-(4-formylbutyl)piperidino, 3-(2-butyrylbutyl)-piperidino, 2-[1-(formylmethyl)ethyl]piperidino, 2-carboxymethyl-piperidino, 2-(1-carboxyethyl)piperidino, 3-(2-carboxypropyl)piperidino, 4-[1-(carboxymethyl)ethyl]piperidino, 2-(4-carboxybutyl)piperidino, 2-methoxycarbonylmethylpiperidino, 2-(2-methoxycarbonylethyl)piperidino, 3-(1-ethoxycarbonylethyl)piperidino, 4-(2-propoxycarbonylpropyl)piperidino, 2-[1-(methoxycarbonylmethyl)ethyl]-piperidino, 2-(4-t-butoxycarbonylbutyl)piperidino or the like;

pyrrolidin-1-yl optionally having $(C_1-C_4)$alkoxy$(C_1-C_4)$alkyl, such as pyrrolidin-1-yl, 2-methoxymethylpyrrolidin-1-yl, 2-(2-methoxyethyl) pyrrolidin-1-yl, 2-(1-ethoxyethyl)pyrrolidin-1-yl, 3-(3-propoxypropyl)pyrrolidin-1-yl, 3-{2-(tert-butoxy)butyl}pyrrolidin-1-yl or the like;

perhydroazepin-1-yl, such as perhydro-1H-azepin-1-yl or the like;

piperazin-1-yl optionally having $(C_1-C_4)$alkyl, such as piperazin-1-yl, 2-methylpiperazin-1-yl, 3-methylpiperazin-1-yl, 4-methylpiperazin-1-yl, 2-ethylpiperazin-1-yl, 3-propylpiperazin-1-yl, 4-isopropylpiperazin-1-yl, 2-butylpiperazin-1-yl, 3-(tert-butyl)piperazin-1-yl or the like;

morpholino;

7-azabicyclo[2.2.1]heptan-7-yl; and 3-azabicyclo[3.2.2]nonan-3-yl or the like, and the most preferred one may include piperidino, 2-methylpiperidino, 2-ethylpiperidino, 3-ethylpiperidino, 4-ethylpiperidino, 2-propylpiperidino, 2,2,6,6-tetramethylpiperidino, 2-hydroxymethylpiperidino, 2-(2-hydroxyethyl) piperidino, 4-(2-hydroxyethyl)piperidino, 2-methoxymethylpiperidino, 2-(2-methoxyethyl) piperidino, 2-acetoxymethylpiperidino, 2-(2-acetoxyethyl)piperidino, 2-ethoxycarbonylpiperidino, 2-carboxypiperidino, 2-(methoxycarbonylmethyl) piperidino, 2-carboxiperidino, 2-carbamoylmethylpiperidino, 2-(N-ethylcarbamoylmethyl)piperidino, 2-N,N-diethylcarbamoylmethyl)piperidino, pyrrolidin-1-yl, 2-methoxymethylpyrrolidin-1-yl, perhydro-1H-azepin-1-yl, 4-methylpiperazin-1-yl, morpholino, 7-azabicyclo-[2.2.1]heptan-7-yl, 3-azabicyclo[3.2.2] nonan-3-yl or the like.

Suitable "aryl" may include phenyl, naphthyl, indenyl, anthryl or the like, and these "aryl" may have one or more suitable substituent(s), such as halogen (e.g. fluoro, chloro, bromo and iodo); lower alkoxy (e.g. methoxy, ethoxy, propoxy, tert-butoxy, pentyloxy, hexyloxy, etc.); nitro; amino; and said protected amino.

The preferred example of "aryl optionally having one or more suitable substituent(s)" may include phenyl which may have 1 to 3 suitable substituent(s) selected from a group consisting of halogen, $(C_1-C_4)$ alkoxy, nitro, amino, $(C_1-C_4)$alkanoylamino, $(C_1-C_4)$ alkoxycarbonylamino, $(C_1-C_4)$ alkanesulfonylamino, $(C_1-C_4)$alkylamino and di$(C_1-C_4)$alkylamino, in which the more preferred one may be phenyl, phenyl having chloro, phenyl having methoxy, phenyl having nitro, phenyl having amino, phenyl having acetylamino, phenyl having methoxycarbonylamino, phenyl having methanesulfonylamino, phenyl having methylamino, and phenyl having dimethylamino.

Suitable "heterocyclic group" may include the ones as exemplified for "nitrogen-containing heterocyclic group" as mentioned above;

unsaturated 3 to 8-membered (preferably 5 or 6-membered) heteromonocyclic group containing one oxygen atom, such as furyl or the like;

unsaturated 3 to 8-membered (preferably 5 or 6-membered) heteromonocyclic group containing one oxygen atom and 1 or 2 sulfur atom(s), such as dihydrooxathiinyl or the like;

unsaturated condensed heterocyclic group containing 1 or 2 sulfur atom(s), such as benzothienyl, benzodithiinyl or the like;

unsaturated condensed heterocyclic group containing one oxygen atom and 1 or 2 sulfur atom(s) such as benzoxathiinyl or the like, in which the preferred one may be unsaturated 3 to 8-membered heteromonocyclic group containing 1 to 4 nitrogen atom(s), and the more preferred one may be pyridyl, and the most preferred one may be 2-pyridyl, 3-pyridyl and 4-pyridyl.

Suitable "lower alkenyl having halogen" may include 1-fluorovinyl, 1-bromovinyl, 1-chloro-2-methylvinyl, 1-bromo-1-propenyl, 2-chloro-2-propenyl, 1-iodo-1-butenyl, 1-bromo-2-methyl-1-propenyl, 3-bromo-1,3-butadienyl, 1-chloro-1-pentenyl, 4-chloro-4-pentenyl, 1-bromo-1-hexenyl or the like.

Suitable "lower alkoxy" may include methoxy, ethoxy, propoxy, isopropoxy, butoxy, tert-butoxy, pentyloxy, hexyloxy or the like.

Suitable "halogen" may include fluoro, chloro, bromo and iodo.

Suitable "leaving group" may include di(lower) alkylamino, such as dimethylamino, diethylamino, N-ethylpropylamino, dibutylamino, N-pentylhexylamino or the like; lower alkoxy such as mentioned above; halogens mentioned above; and lower alkylthio, such as methylthio, ethylthio, propylthio, butylthio, pentylthio, hexylthio or the like.

Suitable "unsaturated heterocyclic group" of said "unsaturated heterocyclic group optionally having one or more suitable substituent(s)" may include unsaturated monocyclic or polycyclic heterocyclic group containing at least one hetero atom, such as nitrogen, oxygen, sulfur or the like.

Suitable examples of said "unsaturated heterocyclic group" may include unsaturated 3 to 8-membered (preferably 5 to 7-membered) heteromonocyclic group containing 1 to 4 nitrogen atom(s), such as azepinyl (e.g. 1H-azepinyl, etc.), pyrrolyl, pyrrolinyl, imidazolyl, pyrazolyl, pyridyl, dihydropyridyl (e.g. 1,2-dihydropyridyl, 1,4-dihydropyridyl, etc.), tetrahydropyridyl (e.g. 1,2,3,6-tetrahydropyridyl, etc.), pyrimidinyl, dihydropyrimidinyl (e.g. 1,2-dihydropyrimidinyl, etc.), pyrazinyl, pyridazinyl, dihydropyridazinyl (e.g. 2,3-dihydropyridazinyl, 1,4-dihydropyridazinyl, etc.), tetrahydropyridazinyl (e.g. 2,3,4,5-tetrahydropyridazinyl, etc.), triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.) or the like;

unsaturated condensed heterocyclic group containing 1 to 4 nitrogen atom(s), such as indolyl, isoindolyl, indolizinyl, benzimidazolyl, quinolyl, dihydroquinolyl (e.g. 2,3-dihydroquinolyl, etc.), isoquinolyl, indazolyl, benzotriazolyl or the like;

unsaturated 3 to 8-membered (preferably 5 or 6-membered) heteromonocyclic group containing 1 or 2 oxygen atom(s) and 1 to 3 nitrogen atom(s), such as oxazolyl, isoxazolyl, dihydroisoxazolyl (e.g. 2,5-dihydroisoxazolyl, etc.), oxadiazolyl (e.g. 1,2,4-oxadiazolyl, 1,3,4-oxadiazolyl, 1,2,5-oxadiazolyl, etc.) or the like;

unsaturated condensed heterocyclic group containing 1 or 2 oxygen atom(s) and 1 to 3 nitrogen atom(s), such as benzoxazolyl, benzoxadiazolyl or the like;

unsaturated 3 to 8-membered (preferably 5 or 6-membered) heteromonocyclic group containing 1 or 2 sulfur atom(s) and 1 to 3 nitrogen atom(s), such as thiazolyl, dihydrothiazolyl (e.g. 2,3-dihydrothiazolyl, etc.), isothiazolyl, thiadiazolyl (e.g. 1,2,3-thiadiazolyl, 1,2,4-thiadiazolyl, 1,3,4-thiadiazolyl, 1,2,5-thiadiazolyl, etc.), dihydrothiadinyl or the like;

unsaturated condensed heterocyclic group containing 1 or 2 sulfur atom(s) and 1 to 3 nitrogen atom(s), such as benzothiazolyl, benzothiadiazolyl (e.g. benzo[d][1,2,3]thiadiazolyl, etc.), imidazothiadiazolyl (e.g. 5H-imidazo[2,1-b][1,3,4]thiadiazolyl, etc.) or the like;

unsaturated 3 to 8-membered (preferably 5 or 6-membered) heteromonocyclic group containing 1 or 2 sulfur atom(s), such as thienyl, dihydrothiynyl or the like;

unsaturated 3 to 8-membered (preferably 5 or 6-membered) heteromonocyclic group containing one oxygen atom, such as furyl or the like;

unsaturated 3 to 8-membered (preferably 5 or 6-membered) heteromonocyclic group containing one oxygen atom and 1 or 2 sulfur atom(s), such as dihydroxathiinyl or the like;

unsaturated condensed heterocyclic group containing 1 or 2 sulfur atom(s), such as benzothienyl and benzodithiinyl or the like; and unsaturated condensed heterocyclic group containing one oxygen atom and 1 or 2 sulfur atom(s) such as benzoxathiinyl or the like; and so on.

Among these, the preferred one may be unsaturated heterocyclic group containing at least one nitrogen atom as a hetero atom, and the more preferred one may be unsaturated 3 to 8-membered heteromonocyclic group containing 1 to 4 nitrogen atom(s) and unsaturated condensed heterocyclic group containing 1 or 2 sulfur atom(s) and 1 to 3 nitrogen atom(s), and the much more preferred one may be pyridazinyl, dihydropyridazinyl, tetrahydropyridazinyl, pyrimidinyl, dihydropyrimidinyl, pyridyl, dihydropyridyl, tetrahydropyridyl, pyrazolyl and imidazothiadiazolyl, and the most preferred one may be pyridazinyl, 2,3-dihydropyridazinyl, 1,4-dihydropyridazinyl, 2,3,4,5-tetrahydropyridazinyl, pyrimidinyl, 1,2-dihydropyrimidinyl, pyridyl, 1,2-dihydropyridyl, 1,4-dihydropyridyl, 1,2,3,6-tetrahdyropyridyl, pyrazolyl and imidazo[2,1-b][1,3,4]thiadiazolyl.

The "unsaturated heterocyclic group" mentioned above may have one or more (preferably 1 to 4) suitable substituent (s), such as lower alkyl (e.g. methyl, ethyl, propyl, isopropyl, butyl, tert-butyl, pentyl and hexyl, etc.) which may have one or more (preferably 1 to 4) suitable substituent(s) as mentioned hereinafter; carboxy(lower)alkenyl (e.g. 1-carboxyvinyl, 2-carboxyvinyl, 1-carboxy-2-propenyl, 3-carboxy-2-propenyl, 3-carboxy-2-butenyl, 4-carboxy-2-methyl-2-butenyl, 3-carboxy-1-hexenyl, etc.); amino; di(lower)alkylamino (e.g. dimethylamino, N-methylethylamino, dipropylamino, N-butyl-(2-methylbutyl)amino, N-pentylhexylamino, etc.); halogens (e.g. fluoro, chloro, bromo, iodo, etc.); lower alkoxy (e.g. methoxy, ethoxy, propoxy, isopropoxy, butoxy, tert-butoxy, pentyloxy, hexyloxy, etc.); oxo; hydroxy; cyano; acyl group as mentioned below or the like.

Suitable "acyl group" may include lower alkanoyl group (e.g. formyl, acetyl, propionyl, butyryl, isobutyryl, pivaloyl, hexanoyl, etc.), carboxy, protected carboxy or the like.

Suitable example of said "protected carboxy" may be esterified carboxy, the preferred one of which may include lower alkoxycarbonyl (e.g. methoxycarbonyl, ethoxycarbonyl, propoxycarbonyl, tert-butoxycarbonyl, pentyloxycarbonyl, hexyloxycarbonyl, etc.) or the like; and amidated carboxy, the preferred one of which may include carbamoyl and N,N-di(lower)alkylcarbamoyl groups, the two lower alkyl groups of which may bond to each other to form a 3 to 6-membered ring (e.g. N,N-dimethylcarbamoyl, N-methyl-N-ethylcarbamoyl, N,N-diethylcarbamoyl, N,N-dipropylcarbamoyl, N-butyl-N-tert-butylcarbamoyl, N,N-dipentylcarbamoyl, N-pentyl-N-hexylcarbamoyl, 1-aziridinylcarbamoyl, 1-azetidinylcarbonyl, 1-pyrrolidinylcarbonyl, piperidinocarbonyl, etc.) or the like.

Suitable example of the "suitable substituent(s)" of said "lower alkyl which may have one or more suitable substituent(s)" may include hydroxy, said halogen, said lower alkoxy, said acyl or the like.

Suitable example of said "lower alkyl group having one or more suitable substituent(s)" may include lower alkyl having both hydroxy and halogen, such as 1-hydroxy-1-chloromethyl, 1-hydroxy-2-chloroethyl, 2-hydroxy-3-fluoropropyl, 2-hydroxy-3,3,3-trichloropropyl, 3-bromo-4-hydroxy-4-iodobutyl, 1-chloro-2-hydroxy-4-fluoropentyl, 3,4-dihydroxy-6-chlorohexyl or the like;

hydroxy(lower)alkyl such as hydroxymethyl, 2-hydroxyethyl, 2-hydroxypropyl, 3-hydroxypropyl, 1-hydroxy-1-methylethyl, 1-hydroxybutyl, 1-hydroxymethyl-1-methylethyl, 3-hydroxypentyl, 2-hydroxyhexyl or the like;

lower alkoxy(lower)alkyl such as methoxymethyl, ethoxymethyl, 2-ethoxyethyl, 1-propoxyethyl, 3-isopropoxypropyl, 2-butoxybutyl, 1-tert-butoxymethyl-1-methylethyl, 5-pentyloxypentyl, hexyloxymethyl, 3-hexyloxyhexyl or the like; and acyl(lower)alkyl, the preferred one of which may be carboxy(lower)alkyl (e.g. carboxymethyl, 2-carboxyethyl, 2-carboxypropyl, 3-carboxypropyl, 2-carboxy-1-methylethyl, 4-carboxybutyl, 1-carboxymethyl-1-methylethyl, 3-carboxypentyl, 2-carboxyhexyl, etc.), preferably protected carboxy (lower)alkyl, such as esterified carboxy(lower)alkyl and amidated carboxy(lower)alkyl, still more preferably lower alkoxycarbonyl(lower)alkyl (e.g. methoxycarbonylmethyl, ethoxycarbonylmethyl, 2-methoxycarbonylethyl, 2-ethoxycarbonylethyl, 1-propoxycarbonylethyl, 3-ethoxycarbonylpropyl, 2-butoxycarbonylbutyl, 4-ethoxycarbonylbutyl, 1-tert-butoxycarbonylmethyl-1-methylethyl, 5-pentyloxycarbonylpentyl, hexyloxycarbonylmethyl, 3-hexyloxycarbonylhexyl, etc.), carbamoyl(lower) alkyl (e.g. carbamoylmethyl, 2-carbamoylethyl, 3-carbamoylpropyl, 2-carbamoyl-1-methylethyl, 4-carbamoylbutyl, 1-carbamoylmethyl-1-methylethyl, 5-carbamoylpentyl, 3-carbamoylhexyl, etc.), and N,N-di(lower)alkylcarbamoyl(lower)alkyl in which two lower alkyl groups on nitrogen atom may bond to each other to form 3 to 6-membered ring [e.g. N,N-dimethylcarbamoylmethyl, 2-(N,N- dimethylcarbamoyl)ethyl, 2-(N-methyl-N-ethylcarbamoyl)ethyl, 3-(N-methyl-N-ethylcarbamoyl) propyl, 2-(N,N-dipropylcarbamoyl)-1-methylethyl, 4-(N,N-dipropylcarbamoyl)butyl, 1-(N,N-dimethylcarbamoyl)methyl-1-methylethyl, 5-(N-pentyl-N-hexylcarbamoyl)pentyl, 3-(N-pentyl-N-hexylcarbamoyl)hexyl, (1-aziridinylcarbonyl)methyl, 2-(1-azetidinylcarbonyl)ethyl, 2-(piperidinocarbonyl) ethyl, 3-(1-pyrrolidinylcarbonyl)propyl, 2-(piperidinocarbonyl)-1-methylethyl, 4-(1-azetidinylcarbonyl)butyl, 1-(1-aziridinylcarbonyl) methyl-1-methylethyl, 3-(1-pyrrolidinylcarbonyl) pentyl, 6-piperidinocarbonyl)hexyl, etc.] or the like.

The preferred substituent on said "unsaturated heterocyclic group" may be lower alkyl, lower alkyl having hydroxy and halogen, hydroxy(lower)alkyl, lower alkoxy(lower) alkyl, carboxy(lower)alkyl, lower alkoxycarbonyl(lower) alkyl, carbamoyl(lower)alkyl, N,N-di(lower) alkylcarbamoyl(lower)alkyl wherein two lower alkyl groups on nitrogen atom may bond to each other to form a 3 to 6-membered ring, carboxy(lower)alkenyl, di(lower) alkylamino, halogen, lower alkoxy, oxo, carboxy, lower alkoxycarbonyl, lower alkanoyl, amino, cyano and hydroxy. Among these, the more preferred one may be ($C_1$–$C_4$)alkyl, ($C_1$–$C_4$)alkyl having hydroxy and halogen, hydroxy($C_1$–$C_4$) alkyl, ($C_1$–$C_4$)alkoxy($C_1$–$C_4$)alkyl, carboxy($C_1$–$C_4$)alkyl, ($C_1$–$C_4$)alkoxycarbonyl($C_1$–$C_4$)alkyl, carbamoyl($C_1$–$C_4$) alkyl, N,N-di($C_1$–$C_4$)alkylcarbamoyl($C_1$–$C_4$)alkyl, piperidinocarbonyl($C_1$–$C_4$)alkyl, carboxy($C_2$–$C_4$)alkenyl, di($C_1$–$C_4$)alkylamino, halogen, ($C_1$–$C_4$)alkoxy, oxo, carboxy, ($C_1$–$C_4$) alkoxycarbonyl, ($C_1$–$C_4$) alkanoyl, amino, cyano and hydroxy. The most preferred one may be methyl, propyl, 2-hydroxy-3,3,3-trichloropropyl, 2-hydroxyethyl, 3-hydroxypropyl, 2-ethoxyethyl, 2-carboxyethyl, 3-carboxypropyl, 4-carboxybutyl, methoxycarbonylmethyl, 2-methoxycarbonylethyl, 3-ethoxycarbonylpropyl, 4-ethoxycarbonylbutyl, 2-carbamoylethyl, 2-(N,N-dimethylcarbamoyl)ethyl, 2-(piperidinocarbonyl)ethyl, 2-carboxyvinyl, dimethylamino, chloro, methoxy, oxo, carboxy, ethoxycarbonyl, methoxycarbonyl, acetyl, amino, cyano and hydroxy.

The "unsaturated heterocyclic group" of said "unsaturated heterocyclic group which may have one or more suitable substituent(s)" may have one or more (preferably 1 to 4) substituent(s) mentioned below in addition to the ones mentioned hereinbefore.

The substituent referred to above may include amino (lower)alkyl; lower alkylamino(lower)alkyl; carboxy(lower) alkylamino(lower)alkyl; protected carboxy(lower) alkylamino(lower)alkyl; lower alkylamino(lower)alkyl having hydroxy and aryloxy; protected amino(lower)alkyl; cyano(lower)alkyl; cyano(higher)alkyl; lower alkyl having heterocyclic group in which heterocyclic group may have one or more suitable substituent(s); higher alkyl having heterocyclic group in which heterocyclic group may have one or more suitable substituent(s); ar(lower)alkyl; lower alkenyl; heterocyclic group which may have one or more suitable substituent(s); cyclo(lower)alkyl which may have one or more suitable substituent(s); and cyclo (lower) alkenyl which may have one or more suitable substituent(s).

These substituents are now explained in the following.

Suitable "amino(lower)alkyl" may include aminomethyl, 1-aminoethyl, 2-aminoethyl, 2-aminopropyl, 3-aminobutyl, 2-amino-1,1-dimethylethyl, 5-aminopentyl, 1-aminohexyl, etc. Among these, the preferred one may be amino($C_1$–$C_4$) alkyl, and the more preferred one may be 2-aminoethyl.

Suitable "lower alkylamino(lower)alkyl" may include mono- or di(lower)alkylamino(lower)alkyl such as methylaminomethyl, 2-(ethylamino)ethyl, 3-(propylamino) propyl, 2-(propylamino)butyl, 2-(t-butylamino)-1,1-dimethylethyl, 4-pentylaminopentyl, 6-hexylaminohexyl, dimethylaminomethyl, 2-dimethylaminoethyl, 1-(N-methylethylamino)ethyl, 1-dimethylaminopropyl, 2-diethylaminopropyl, 3-dimethylaminopropyl, 3-(N-propylbutylamino)butyl, 4-dimethylaminobutyl, 2-dibutylamino-1,1-dimethylethyl, 4-dipentylaminopentyl, 6-(N-pentylhexylamino)hexyl or the like. Among these, preferred one may be di(lower)alkylamino(lower)alkyl, and the more preferred one may be di($C_1$–$C_4$)alkylamino ($C_1$–$C_4$)alkyl, and the most preferred one may be 2-dimethylaminoethyl, 3-dimethylaminopropyl or 5 4-dimethylaminobutyl.

Suitable "carboxy(lower)alkylamino(lower)alkyl" may include carboxymethylaminomethyl, 2-(carboxymethylamino)ethyl, 2-(1-carboxyethylamino) ethyl, 3-(2-carboxypropylamino)propyl, 2-(3-carboxypropylamino)butyl, 2-(2-carboxy-1,1-dimethylethylamino)-1,1-dimethylethyl, 4-(5-carboxypentylamino)pentyl, 6-(3-carboxyhexylamino)hexyl or the like, in which the preferred one may be carboxy ($C_1$–$C_4$)alkylamino($C_1$–$C_4$)alkyl, and the most preferred one may be 2-(carboxymethylamino)ethyl.

Suitable "protected carboxy" of said "protected carboxy (lower)alkylamino(lower)alkyl" may be esterified carboxy or the like, and concrete example of the ester moiety in said esterified carboxy may include lower alkyl esters (e.g. methyl ester, ethyl ester, propyl ester, isopropyl ester, butyl ester, isobutyl ester, tert-butyl ester, pentyl ester, hexyl ester, 1-cyclopropylethyl ester, etc.) which may have suitable substituent(s), for example, lower alkanoyloxy(lower)alkyl ester (e.g. acetoxymethyl ester, propionyloxymethyl ester, butyryloxymethyl ester, valeryloxymethyl ester, pivaloyloxymethyl ester, 1-acetoxyethyl ester, 1-propionyloxyethyl ester, 2-propionyloxyethyl ester, hexanoyloxymethyl ester, etc.), lower alkanesulfonyl(lower)alkyl ester (e.g. 2-mesylethyl ester etc.) or mono(or di or tri)halo(lower) alkyl ester (e.g. 2-iodoethyl ester, 2,2,2-trichloroethyl ester, etc.); lower alkenyl ester (e.g. vinyl ester, allyl ester, etc.); lower alkynyl ester (e.g. ethynyl ester, propynyl ester, etc.); ar(lower)alkyl ester (e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-tert-butylbenzyl ester, etc.) which may have suitable substituent(s); and aryl ester (e.g. phenyl ester, 4-chlorophenyl ester, tolyl ester, 4-tert-butylphenyl ester, xylyl ester, mesityl ester, cumenyl ester, etc.) which may have suitable substituent(s), or the like.

Suitable "protected carboxy(lower)alkylamino(lower) alkyl" may include esterified carboxy(lower)alkylamino (lower)alkyl in which the preferred one may be lower alkoxycarbonyl(lower)alkylamino(lower)alkyl, such as methoxycarbonylmethylaminomethyl, 2-(ethoxycarbonylmethylamino)ethyl, 2-(1-ethoxycarbonylethylamino)ethyl, 3-(2-propoxycarbonylpropylamino)propyl, 2-(3-butoxycarbonylpropylamino)butyl, 2-(2-t-butoxycarbonyl-1,1-dimethylethylamino)-1,1-dimethylethyl, 4-(5-pentyloxycarbonylpentylamino)pentyl, 6-(3-hexyloxycarbonylhexylamino)hexyl or the like. The more preferred one may be ($C_1$–$C_4$)alkoxycarbonyl($C_1$–$C_4$) alkylamino($C_1$–$C_4$)alkyl, and the most preferred one may be 2-(ethoxycarbonylmethylamino)ethyl.

Suitable "lower alkylamino(lower)alkyl having hydroxy and aryloxy" may include said "lower alkylamino(lower)

alkyl" having "hydroxy" and "aryloxy" (e.g. phenoxy, tolyloxy, naphthyloxy, etc.), the suitable example of which may include 1-(1-naphthyloxy)-1-hydroxymethylaminomethyl, 2-(1-hydroxy-2-phenoxyethylamino)ethyl, 2-[2-hydroxy-3-(1-naphthyloxy) propylamino]ethyl, 2-[4-hydroxy-3-(p-tolyloxy) butylamino]propyl, 2-[4-hydroxy-1-(2-naphthyloxy) butylamino]-1,1-dimethylethyl, 4-[1-hydroxy-5-(1-naphthyloxy)pentylamino]pentyl and 6-[2-hydroxy-4-(2-naphthyloxy)hexylamino]hexyl, in which the preferred one may be $(C_1-C_4)$alkylamino$(C_1-C_4)$alkyl having hydroxy and naphthyloxy, and the more preferred one may be 2-[2-hydroxy-3-(1-naphthyloxy)propylamino]ethyl.

Suitable "protected amino(lower)alkyl" may. include acylamino(lower)alkyl.

Suitable example of said acylamino may be lower alkanoylamino (e.g. formylamino, acetylamino, propionylamino, hexanoylamino, pivaloylamino, etc.), mono (or di or tri)halo(lower) alkanoylamino (e.g. chloroacetylamino, trifluoroacetylamino, etc.), lower alkoxycarbonylamino (e.g. methoxycarbonylamino, ethoxycarbonylamino, tert-butoxycarbonylamino, tert-pentyloxycarbonylamino, hexyloxycarbonylamino, etc.), mono(or di or tri)halo(lower)alkoxycarbonylamino (e.g. chloromethoxycarbonylamino, dichloroethoxycarbonylamino, trichloroethoxycarbonylamino, etc.), aroylamino (e.g. benzoylamino, toluoylamino, xyloylamino, naphthoylamino, etc.), ar(lower)alkanoylamino such as phenyl(lower)alkanoylamino (e.g. phenylacetylamino, phenylpropionylamino, etc.), aryloxycarbonylamino (e.g. phenoxycarbonylamino, naphthyloxycarbonylamino, etc.), aryloxy(lower)alkanoylamino such as phenoxy(lower) alkanoylamino (e.g. phenoxyacetylamino, phenoxypropionylamino, etc.), arylglyoxyloylamino (e.g. phenylglyoxyloylamino, naphthylglyoxyloylamino, etc.), ar(lower)alkoxycarbonylamino which may have suitable substituent(s), such as phenyl(lower)alkoxycarbonylamino which may have nitro or lower alkoxy (e.g. benzyloxycarbonylamino, phenethyloxycarbonylamino, p-nitrobenzyloxycarbonylamino, p-methoxybenzyloxycarbonylamino, etc.) thienylacetylamino, imidazolylacetylamino, furylacetylamino, tetrazolylacetylamino, thiazolylacetylamino, thiadiazolylacetylamino, thienylpropionylamino, thiadiazolylpropionylamino, lower alkylsulfonylamino (e.g. methylsulfonylamino, ethylsulfonylamino, propylsulfonylamino, isopropylsulfonylamino, pentylsulfonylamino, butylsulfonylamino, etc.), arylsulfonylamino (e.g. phenylsulfonylamino, tolylsulfonylamino, xylylsulfonylamino, naphthylsulfonylamino, etc.), ar(lower) alkylsulfonylamino such as phenyl(lower) alkylsulfonylamino (e.g. benzylsulfonylamino, phenethylsulfonylamino, benzhydrylsulfonylamino, etc.), and imido (e.g. 1,2-cyclohexanedicarboximido, succinimido, phthalimido, etc.) or the like.

Preferred example of said "protected amino(lower)alkyl" may be imido(lower)alkyl, such as phthalimidomethyl, 2-phthalimidoethyl, 1-(1,2-cyclohexanedicarboximido) ethyl, 2-succinimidopropyl, 3-phthalimidobutyl, 2-(1,2-cyclohexanedicarboximido)-1,1-dimethylethyl, 5-phthalimidopentyl, 1-phthalimidohexyl or the like. The more preferred one may be imido $(C_1-C_4)$ alkyl, and the most preferred one may be 2-phthalimidoethyl.

Suitable "cyano(lower)alkyl" may include cyanomethyl, 1-cyanoethyl, 2-cyanoethyl, 3-cyanopropyl, 2-cyanobutyl, 4-cyanobutyl, 2-cyano-1,1-dimethylethyl, 4-cyanopentyl, 5-cyanopentyl, 6-cyanohexyl or the like, in which the preferred one may be cyano $(C_1-C_6)$alkyl, and the most preferred one may be cyanomethyl, 2-cyanoethyl, 3-cyanopropyl, 4-cyanobutyl, 5-cyanopentyl and 6-cyanohexyl.

Suitable "cyano(higher)alkyl" may include 7-cyanoheptyl, 8-cyanooctyl, 4-cyanooctyl, 8-cyano-3-methylheptyl, 9-cyanononyl, 1-cyanononyl, 10-cyanodecyl, 8-cyanoundecyl, 12-cyanododecyl, 11-cyano-4-methylundecyl, 13-cyanotridecyl, 6-cyanotetradecyl, 15-cyanopentadecyl, 12-cyanohexadecyl, 17-cyanoheptadecyl, 4-cyanooctadecyl, 19-cyanononadecyl, 1-cyano-12-ethylheptadecyl, 20-cyanoeicosyl or the like, in which the preferred one may be cyano$(C_7-C_{16})$alkyl and the more preferred one may be 7-cyanoheptyl, 8-cyanooctyl, 9-cyanononyl, 10-cyanodecyl and 12-cyanodecyl.

Suitable "lower alkyl" may include straight-chain or branched-chain alkyl such as methyl, ethyl, propyl, isopropyl, butyl, t-butyl, pentyl, hexyl or the like.

Suitable "lower alkenyl" may include straight-chain or branched-chain alkenyl such as vinyl, allyl, 2-butenyl, 2-methyl-2-propenyl, 4-pentenyl, 3-hexenyl or the like, in which the preferred one may be $(C_2-C_4)$ alkenyl, and the more preferred one may be vinyl.

Suitable "lower alkyl" of said "lower alkyl having heterocyclic group, in which heterocyclic group may have one or more suitable substituent(s)" may include the same lower alkyl as mentioned above, and the preferred one may be $(C_1-C_6)$ alkyl, and the most preferred one may be methyl, ethyl, propyl, butyl, pentyl and hexyl.

Suitable "higher alkyl" of said "higher alkyl having a heterocyclic group, in which heterocyclic group may have one or more suitable substituent(s)" may include heptyl, octyl, 3-methylheptyl, nonyl, 2,6-dimethylheptyl, decyl, undecyl, dodecyl, 4-methyldodecyl, tridecyl, tetradecyl, pentadecyl, hexadecyl, heptadecyl, octadecyl, nonadecyl, 12-ethylheptadecyl, eicosyl or the like, in which the preferred one may be $(C_7-C_{16})$alkyl, and the more preferred one may be heptyl, octyl, nonyl, decyl and dodecyl.

Suitable "heterocyclic group" of said "lower alkyl having a heterocyclic group, in which heterocyclic group may have one or more suitable substituent(s)" and of said "higher alkyl having heterocyclic group, in which heterocyclic group may have one or more suitable substituent(s)" may include saturated or unsaturated monocyclic or polycyclic heterocyclic group containing at least one hetero atom such as oxygen, sulfur, nitrogen or the like. The particularly preferred heterocyclic group may be 3 to 8-membered unsaturated heteromonocyclic group containing 1 to 4 nitrogen atom(s), such as pyrrolyl, pyrrolinyl, imidazolyl, pyrazolyl, pyridyl and its N-oxide, pyrimidyl, pyrazinyl, pyridazinyl, triazolyl (e.g. 4H-1,2,4-triazolyl, 1H-1,2,3-triazolyl, 2H-1, 2,3-triazolyl, etc.), tetrazolyl (e.g. 1H-tetrazolyl, 2H-tetrazolyl, etc.), dihydrotriazinyl (e.g. 4,5-dihydro-1,2, 4-triazinyl, 2,5-dihydro-1,2,4-triazinyl, etc.) or the like;

3 to 8-membered saturated heteromonocyclic group containing 1 to 4 nitrogen atom(s), such as pyrrolidinyl, imidazolidinyl, piperidyl (e.g. piperidino, etc.), piperazinyl or the like;

unsaturated condensed heterocyclic group containing 1 to 5 nitrogen atom(s), such as indolyl, isoindolyl, indolizinyl, benzimidazolyl, quinolyl, isoquinolyl, indazolyl, benzotriazolyl, tetrazolopyridyl, tetrazolopyridazinyl (e.g. tetrazolo[1,5-b]pyridazinyl etc.), dihydrotriazolopyridazinyl or the like;

3 to 8-membered unsaturated heteromonocyclic group containing 1 or 2 oxygen atom(s) and 1 to 3 nitrogen atom(s), such as oxazolyl, isoxazolyl, oxadiazolyl (e.g. 1,2,4-oxadiazolyl, 1,3,4-oxadiazolyl, 1,2,5-oxadiazolyl, etc.) or the like;

3 to 8-membered saturated heteromonocyclic group containing 1 or 2 oxygen atom(s) and 1 to 3 nitrogen atom(s), such as morpholinyl, oxazolidinyl (e.g. 1,3-oxazolidinyl etc.) or the like;

unsaturated condensed heterocyclic group containing 1 or 2 oxygen atom(s) and 1 to 3 nitrogen atom(s), such as benzoxazolyl, benzoxadiazolyl or the like;

3 to 8-membered unsaturated heteromonocyclic group containing 1 or 2 sulfur atom(s) and 1 to 3 nitrogen atom(s), such as 1,3-thiazolyl, 1,2-thiazolyl, thiazolinyl, thiadiazolyl (e.g. 1,2,4-thiadiazolyl, 1,3,4-thiadiazolyl, 1,2,5-thiadiazolyl, 1,2,3-thiadiazolyl) or the like;

3 to 8-membered saturated heteromonocyclic group containing 1 or 2 sulfur atom(s) and 1 to 3 nitrogen atom(s), such as thiazolidinyl or the like;

3 to 8-membered unsaturated heteromonocyclic group containing one sulfur atom, such as thienyl or the like;

unsaturated condensed heterocyclic group containing 1 or 2 sulfur atom(s) and 1 to 3 nitrogen atom(s), such as benzothiazolyl, benzothiadiazolyl or the like;

3 to 8-membered unsaturated heteromonocyclic group containing 1 or 2 oxygen atom(s), such as furyl, pyranyl, dioxolyl or the like;

3 to 8-membered saturated heteromonocyclic group containing 1 or 2 oxygen atom(s), such as oxolanyl, tetrahydropyranyl (e.g. tetrahydro-2H-pyran-2-yl etc.), dioxolanyl or the like;

unsaturated condensed heterocyclic group containing 1 or 2 oxygen atom(s), such as isobenzofuranyl, chromenyl (e.g. 2H-chlomen-3-yl etc.), dihydrochromenyl (e.g. 3,4-dihydro-2H-chlomen-4-yl etc.)or the like; and so on.

Preferred example of said "heterocyclic group" may be 3 to 8-membered unsaturated heteromonocyclic group containing 1 to 4 nitrogen atom(s); 3 to 8-membered saturated heteromonocyclic group containing 1 to 4 nitrogen atom(s), 3 to 8-membered saturated heteromonocyclic group containing 1 or 2 oxygen atom(s) and 1 to 3 nitrogen atom(s); and 3 to 8-membered saturated heteromonocyclic group containing 1 or 2 oxygen atom(s), in which the preferred one may be pyridyl, tetrazolyl, piperidyl, piperazinyl, morpholinyl, oxazolidinyl and tetrahydropyranyl, and the more preferred one may be 4-pyridyl, 1H-tetrazol-5-yl, piperidino, 1-piperazinyl, morpholino, 1,3-oxazolidin-5-yl and tetrahydro-2H-pyran-2-yl.

The "heterocyclic group" mentioned above may have one or more (preferably 1 to 3) suitable substituent(s) such as hydroxy(lower)alkyl (e.g. hydroxymethyl, 2-hydroxyethyl, 1-hydroxypropyl, 4-hydroxybutyl, 2-hydroxy-1,1-dimethylethyl, 3-hydroxypentyl, 6-hydroxyhexyl, etc.), aryl optionally having lower alkoxy (e.g. phenyl, naphthyl, 2-methoxyphenyl, 2-methoxynaphthyl, 3-ethoxyphenyl, 4-propoxyphenyl, 2-butoxyphenyl, 5-propoxynaphthyl, 3-t-butoxyphenyl, 4-pentyloxyphenyl, 2-hexyloxyphenyl, etc.), oxo or the like. The preferred one, among such "suitable substituent(s)", may be hydroxy($C_1$–$C_4$)alkyl, phenyl having ($C_1$–$C_4$)alkoxy, and oxo, and the more preferred one may be 2-hydroxyethyl, 2-methoxyphenyl and oxo.

Suitable "heterocyclic group" of said "heterocyclic group which may have one or more suitable substituent(s)" may include the same groups as mentioned for the "heterocyclic group" of said "lower alkyl having heterocyclic group, in which heterocyclic group may have one or more suitable substituent(s)" and of said "higher alkyl having a heterocyclic group, in which heterocyclic group may have one or more suitable substituent(s)", and the preferred one may be unsaturated condensed heterocyclic group containing 1 or 2 oxygen atom(s) and the more preferred one may be dihydrochromenyl, and the most preferred one may be 3,4-dihydro-2H-chromen-4-yl.

This "heterocyclic group" may have one or more (preferably 1 to 4) suitable substituent(s) such as said lower alkyl, hydroxy, cyano or the like, in which the preferred one may be ($C_1$–$C_4$)alkyl, hydroxy and cyano, and the most preferred one may be methyl, hydroxy and cyano.

Suitable "ar(lower)alkyl" may include mono- or di- or tri-phenyl(lower)alkyl (e.g. benzyl, phenethyl, 2-phenylpropyl, 4-phenylbutyl, 2-phenyl-1,1-dimethylethyl, 1-phenylpentyl, 6-phenylhexyl, benzhydryl, trityl, etc.) or the like, in which the preferred one may be phenyl($C_1$–$C_4$) alkyl, and the most preferred one may be benzyl.

Suitable "nitrogen-containing heterocyclic group" of said "nitrogen-containing heterocyclic group which may have one or more suitable substituent(s)" may include heterocyclic group containing at least one nitrogen atom as its ring member among said "heterocyclic group", and this "nitrogen-containing heterocyclic group" may have one or more (preferably 1 to 3) suitable substituent(s) (e.g. said hydroxy(lower)alkyl, said aryl which may have lower alkoxy, oxo, etc.).

Suitable "tetrazolyl(lower)alkyl" may include 1H-tetrazol-5-ylmethyl, 2-(1H-tet-razol-5-yl)ethyl, 3-(1H-tetrazol-5-yl)propyl, 4-(1H-tetrazol-5-yl)butyl, 2-(2H-tetrazol-2-yl)-1,1-dimethylethyl, 4-(1H-tetrazol-1-yl)pentyl, 5-(1H-tetrazol-5-yl)pentyl, 6-(1H-tetrazol-5-yl)hexyl or the like, in which the preferred one may be tetrazolyl($C_1$–$C_4$) alkyl, and the more preferred one may be (1H-tetrazol-5-yl)methyl, 2-(1H-tetrazol-5-yl)ethyl, 3-(1H-tetrazol-5-yl)propyl, 4-(1H-tetrazol-5-yl)butyl, 5-(1H-tetrazol-5-yl)pentyl, and 6-(1H-tetrazol-5-yl)hexyl.

Suitable "tetrazolyl(higher)alkyl" may include 7-(1H-tetrazol-5-yl)heptyl, 8-(1H-tetrazol-5-yl)octyl, 4-(1H-tetrazol-1-yl)octyl, 8-(1H-tetrazol-5-yl)-3-methylheptyl, 9-(1H-tetrazol-5-yl)nonyl, 1-(1H-tetrazol-1-yl)nonyl, 10-(1H-tetrazol-5-yl)decyl, 8-(1H-tetrazol-5-yl)undecyl, 12-(1H-tetrazol-5-yl)dodecyl, 11-(1H-tetrazol-5-yl)-4-methylundecyl, 13-(1H-tetrazol-5-yl)tridecyl, 6-(1H-tetrazol-5-yl)-tetradecyl, 15-(1H-tetrazol-5-yl)-pentadecyl, 12-(1H-tetrazol-5-yl)-hexadecyl, 17-(1H-tetrazol-1-yl)-heptadecyl, 4-(1H-tetrazol-5-yl)-octadecyl, 19-(1H-tetrazol-5-yl)-nonadecyl, 1-(1H-tetrazol-1-yl)-12-ethylheptadecyl, 20-(1H-tetrazol-5-yl)eicosyl or the like, in which the preferred one may be tetrazolyl($C_7$–$C_{16}$)alkyl, and the more preferred one may be 7-(1H-tetrazol-5-yl)heptyl, 8-(1H-tetrazol-5-yl)-octyl, 9-(1H-tetrazol-5-yl)nonyl, 10-(1H-tetrazol-5-yl)decyl and 12-(1H-tetrazol-5-yl)dodecyl.

Suitable "cyclo(lower)alkyl" may include cyclo($C_3$–$C_8$) alkyl such as cyclopropyl, cyclobutyl, cyclopentyl, cyclohexyl, cycloheptyl, cyclooctyl or the like, in which the preferred one may be cyclo($C_5$–$C_7$)alkyl such as cyclopentyl, cyclohexyl, cycloheptyl or the like.

The "cyclo(lower)alkyl" mentioned above may have one or more (preferably 1 to 3) suitable substituent(s) selected from among acyl(lower)alkyl, acyl(lower)alkylidene or the like.

Suitable "cyclo(lower)alkenyl" may include cyclo($C_3$–$C_8$)alkenyl such as cyclopropenyl, cyclobutenyl, cyclopentenyl, cyclohexenyl, cycloheptenyl, cyclooctenyl or the like, in which the preferred one may be cyclo($C_5$–$C_7$) alkenyl such as cyclopentenyl, cyclohexenyl, cycloheptenyl or the like, and the more preferred one may be cyclohexenyl or cycloheptenyl.

The "cyclo(lower)alkenyl" mentioned above may also have one or more (preferably 1 to 3) suitable substituents such as those mentioned above for "cyclo(lower)alkyl".

Suitable example of the above "acyl(lower)alkyl" may include carboxy(lower)alkyl (e.g. carboxymethyl, 2-carboxyethyl, 3-carboxypropyl, 1-carboxymethylethyl, 4-carboxybutyl, 2-carboxymethyl-2-methylethyl, 5-carboxypentyl, 3-carboxyhexyl, etc.) and lower alkanoyl (lower)alkyl (e.g. acetylmethyl, formylmethyl, 2-acetylethyl, 2-propionylpropyl, 4-butyrylbutyl, 3-pentanoylpentyl, 6-hexanoylhexyl, etc.), in which the preferred one may be carboxy($C_1$–$C_4$)alkyl or ($C_1$–$C_4$) alkanoyl ($C_1$–$C_4$)alkyl, and the more preferred one may be carboxymethyl, 2-carboxyethyl, 3-carboxypropyl or acetylmethyl.

Other preferred example of "acyl(lower)alkyl", may include protected carboxy(lower)alkyl, in which the preferred one may be esterified carboxy(lower)alkyl, and the more preferred one may be lower alkoxycarbonyl(lower)alkyl (e.g. methoxycarbonylmethyl, ethoxycarbonylmethyl, 2-ethoxycarbonylethyl, 1-propoxycarbonylpropyl, 2-isopropoxycarbonylpropyl, butoxycarbonylmethyl, t-butoxycarbonylmethyl, 4-isobutoxycarbonylbutyl, 3-pentyloxycarbonylpentyl, 6-hexyloxycarbonylhexyl, (1-cyclopropylethoxycarbonyl)methyl, etc.) and phenyl (lower)alkoxycarbonyl(lower)alkyl (e.g. benzyloxycarbonylmethyl, 2-benzyloxycarbonylethyl, 1-phenethyloxycarbonylethyl, 3-benzyloxycarbonylpropyl, 2-benzyloxycarbonylbutyl, 2-phenethyloxycarbonylmethyl-2-methylethyl, 3-benzyloxycarbonylpentyl, 6-benzyloxycarbonylhexyl, etc.), and the more preferred one may be ($C_1$–$C_4$)alkoxycarbonyl($C_1$–$C_4$)alkyl or phenyl ($C_1$–$C_4$)alkoxycarbonyl($C_1$–$C_4$)alkyl, and the particularly preferred one may be methoxycarbonylmethyl, ethoxycarbonylmethyl, t-butoxycarbonylmethyl, 2-benzyloxycarbonylethyl and 3-benzyloxycarbonylpropyl.

Suitable example of "acyl(lower)alkylidene" may include carboxy(lower)alkylidene (e.g. carboxymethylene, 2-carboxyethylidene, 2-carboxypropylidene, 4-carboxybutylidene, 5-carboxypentylidene, 3-carboxyhexylidene, etc.), in which the preferred one may be carboxy($C_1$–$C_4$)alkylidene, and the more preferred one may carboxymethylene.

Other suitableexample of "acyl(lower)alkylidene" may include protected carboxy(lower)alkylidene, in which the preferred one may be esterified carboxy(lower)alkylidene, and the more preferred one may be lower alkoxycarbonyl (lower)alkylidene such as methoxycarbonylmethylene, ethoxycarbonylmethylene, 2-ethoxycarbonylethylidene, 1-propoxycarbonylpropylidene, 2-isopropoxycarbonylpropylidene, butoxycarbonylmethylene, t-butoxycarbonylmethylene, 4-isobutoxycarbonylbutylidene, 3-pentyloxycarbonylpentylidene, 6-hexyloxycarbonylhexylidene, (1-cyclopropylethoxycarbonyl)methylene or the like. The further more preferred one may be ($C_1$–$C_4$)alkoxycarbonyl ($C_1$–$C_4$)alkylidene, and the particularly preferred one may be methoxycarbonylmethylene, ethoxycarbonylmethylene and t-butoxycarbonylmethylene.

Among the pyrazolopyridine compound (I) described above, the particularly preferred compound for practicing the present invention may include the following ones.

(1) (2R)-1-[3-(2-Phenylpyrazolo[1,5-a]pyridin-3-yl) acryloyl]-2-(2-hydroxyethyl)piperidine (trans-isomer)
(2) 3-[2-(3-Carboxypropyl)-3-oxo-2,3-dihydropyridazin-6-yl]-2-phenylpyrazolo[1,5-a]pyridine
(3) (2R)-1-[3-(2-Phenylpyrazolo[1,5-a]pyridin-3-yl) acryloyl]-2-(carboxymethyl)piperidine (trans-isomer)
(4) 3-[2-(2-Carboxymethyl-1-cyclohexenyl)-3-oxo-2,3-dihydropyridazin-6-yl]-2-phenylpyrazolo[1,5-a]pyridine As other specific examples of the adenosine $A_1$ antagonist, xanthine compounds of the following general formula (II) and salts thereof can be mentioned.

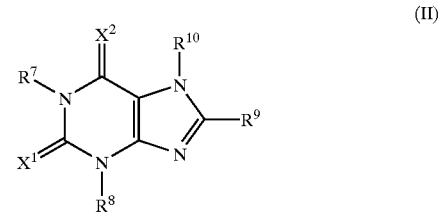

(II)

[wherein $R^7$, $R^8$, and $R^{10}$ each independently is hydrogen, a lower aliphatic hydrocarbon group which may have one or more suitable substituent(s), higher alkyl which may have one or more suitable substituent(s), or ar(lower)alkyl which may have one or more suitable substituent(s), $R^9$ is hydrogen; alicyclic group, aryl, heterocyclic group, alicyclyl (lower)alkyl, ar(lower)alkyl or a heterocyclic(lower)alkyl, each of which may have one or more substituent(s); or a group of the formula:

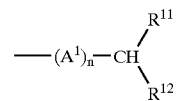

(wherein $R^1$ and $R^2$ each independently isalicyclic group which may have one or more suitable substituent(s) or aryl which may have one or more suitable substituent(s), $A_1$ is lower alkylene, and n is 0 or 1 ), and X and $X^2$ each independently is an oxygen atom or a sulfur atom] (exclusive of caffeine and pentoxiphylline).

Suitable salt of the above xanthine compound may include salts of the kinds mentioned hereinbefore with reference to pyrazolopyridine compound (I).

The xanthine compound (II) includes all the compounds described in EP 0386675, EP 0415456, Japanese laid-open H2-247180, and WO 90/12797. Therefore, the respective groups of compound (II) include all the corresponding groups of the compounds described in the above literature.

The following definitions pertain to particularly preferred examples of the compound (II).

Suitable "lower aliphatic hydrocarbon group" of said "lower aliphatic hydrocarbon group which may have one or more suitable substituent(s)" may include the same lower alkyl, lower alkenyl and lower alkynyl as mentioned for the pyrazolopyridine compound (I).

The above "lower aliphatic hydrocarbon group" may have one or more (preferably 1 to 3) suitable substituent(s), such as, for example, hydroxy, amino, the halogen mentioned for compound (I), and the aryl mentioned for compound (I).

The preferred example of the above "lower aliphatic hydrocarbon group" may be ($C_1$–$C_4$)alkyl, ($C_2$–$C_4$)alkenyl and ($C_2$–$C_4$)alkynyl, and the more preferred one may be ($C_1$–$C_4$)alkyl, and the most preferred one may be propyl.

Suitable "higher alkyl" of "higher alkyl which may have one or more suitable substituent(s)" may include the same groups as mentioned for compound (I), and this "higher alkyl" may have one or more (preferably 1 to 3) suitable substituent(s) such as those mentioned herein above for "lower aliphatic hydrocarbon group".

Suitable "ar(lower)alkyl" may include the same groups as mentioned for compound (I).

This "ar(lower)alkyl" may have one or more (preferably 1 to 3) suitable substituent(s) such as said lower alkyl, said halogen, hydroxy, and said lower alkoxy or the like.

Suitable "alicyclic group" and suitable "alicyclic moiety" of said "alicyclic(lower)alkyl" may include cyclo($C_3$–$C_8$) alkyl such as cyclopropyl, cyclobutyl, cyclopentyl, cyclohexyl, cycloheptyl and cyclooctyl [particularly preferred one may be cyclo ($C_3$–$C_6$) alkyl]; ($C_7$–$C_{12}$) bicycloalkyl or ($C_7$–$C_{12}$)bicycloalkenyl groups [particularly preferred one may be groups of the formula

(wherein --------- represents a single bond or a double bond), groups of the formula:

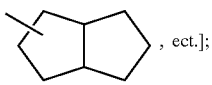

, ect.];

($C_7$–$C_{12}$)tricycloalkyl [particularly preferred one may be groups of the formula:

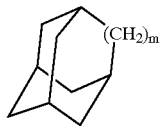

(wherein m is 0 or 1)], or the like.

Suitable "heterocyclic group" and suitable "heterocyclic moiety" of said "heterocyclic(lower)alkyl" may include the same groups as mentioned for the "heterocyclic group" in the description of the compound (I).

Suitable "aryl" may include the same groups as mentioned for compound (I).

The preferred "lower alkyl" of said "alicyclic(lower) alkyl" and of said "heterocyclic(lower)alkyl" may include the same groups as mentioned above for "lower alkyl".

The alicyclic group, aryl, heterocyclic group, alicyclic (lower)alkyl, ar(lower)alkyl and heterocyclic(lower)alkyl for $R^9$ may each have one or more (preferably 1 to 3) suitable substituent(s), such as oxo, hydroxy, amino, said lower alkyl, carboxy, and the protected carboxy mentioned for compound (I) hereinbefore.

The "alicyclic group" and "aryl" mentioned for $R^{11}$ and $R^{12}$ may each have one or more (preferably 1 to 3) suitable substituent(s), such as said lower alkyl, hydroxy, the lower alkoxy mentioned for compound (I) said halogen, amino, nitro or the like.

Suitable "lower alkylene" may include methylene, ethylene, 1-methylethylene, trimethylene, tetramethylene, pentamethylene, hexamethylene or the like, and the preferred one may be ($C_1$–$C_4$)alkylene.

The preferred example of the xanthine compound (II) may be as follows.

$R^7$ and $R^8$ each is preferably lower alkyl, more preferably ($C_1$–$C_4$)alkyl, and most preferably propyl.

The preferred $R^9$ may include cyclo($C_3$–$C_8$)alkyl which may have oxo; ($C_7$–$C_{12}$)tricycloalkyl; and groups of the formula:

(wherein $R^{11}$ and $R^{12}$ each is cyclo($C_3$–$C_8$)alkyl).

The more preferred one may be cyclo($C_3$–$C_6$)alkyl which may have oxo; groups of the formula:

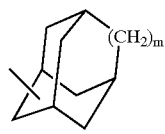

(wherein m is as defined above); and groups of the formula:

(wherein $R^{11}$ and $R^{12}$ each is cyclo($C_3$–$C_6$)alkyl); and the most preferred one may be cyclopentyl having oxo; groups of the formula:

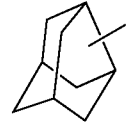

and groups of the formula:

(wherein $R^{11}$ and $R^{12}$ each is cyclopropyl).

Preferably, $R^{10}$ is hydrogen.

Preferably, $X^1$ and $X^2$ each is an oxygen atom.

Among the xanthine compound (II) described above, the particularly preferred compound for the practice of the present invention may include the following ones.

(1) 8-(Noradamantan-3-yl)-1,3-dipropylxanthine
(2) 8-Cyclopentyl-1,3-dipropylxanthine The pharmaceutical composition suited for the practice of the present invention may be the bulk of adenosine $A_1$ antagonist or a salt thereof, or in the form of a solid, semisolid or liquid pharmaceutical preparation containing said antagonist or salt thereof as an active ingredient together with an organic or inorganic carrier or excipient suitable for rectal administration, oral or parenteral (inclusive of subcutaneous, intravenous and intramuscular) administration, intratesticular administration, intraurethral administration, intradeferential administration, intrascrotal administration, administration into the female reproductive organ (e.g. intravaginal administration, intrauterine administration, etc.), administration to the ejaculated seminal fluid in various artificial insemination procedures, administration to sperm in the presence of ova in vitro fertilization, or inhalation. The active ingredient can be compounded with the conventional nontoxic, pharmaceutically acceptable carriers for use in the preparation of tablets, pellets, troches, capsules, suppositories, aerosols, powders for inhalation, solutions, emulsions, suspensions and any other form suitable for use. Where necessary, adjuvants (auxiliary agents), stabilizers, thickeners, coloring agents and perfumes can be used. The adenosine $A_1$ antagonist or its salt can be contained in the pharmaceutical preparation at a sufficient level to produce an expected therapeutic effect according to the course or status of disease.

The pharmaceutical preparations for use in the practice of the present invention can be manufactured by the procedures established in the art. Where necessary, the techniques used in the art for enhancing the bioavailability of drugs can also be applied to the manufacture of the pharmaceutical preparations of the invention.

When a preparation of the invention is applied in an infertile man, it is preferably administered by the intravenous (inclusive of addition to an infusion), intramuscular, oral, intratesticular, intraurethral, intradeferential or intrascrotal route, or into the female reproductive organ, or to ejaculated seminal fluids in various artificial insemination procedures or to sperm in the presence of ova in vitro fertilization.

The therapeutically effective dose of the adenosine $A_1$ antagonist varies with the patient's age and other factors, but for the tretament of male sterility, 0.01–200 mg, as the adenosine $A_1$ antagonist, per kilogram body weight can be administered daily.

The preparation may also be administered for the prophylaxis of male sterility. Furthermore, it is also expected to find application in female infertility as well as in male sterility. In addition, its utilization as an in vitro diagnostic reagent for sperm function testing is also expected.

What is claimed is:

1. A method for treating infertility or treating male sterility comprising:

selecting a subject in need thereof, contacting sperm in said subject with an amount of an adenosine $A_1$ antagonist effective for inducing a sperm acrosomal reaction, and contacting said sperm with an ovum, wherein said adenosine $A_1$ antagonist is a pyrazolopyridine compound of the following general formula or a salt thereof:

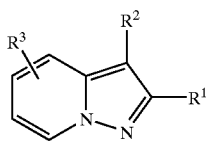

wherein $R^1$ is lower alkyl, aryl which may have one or more suitable substituent(s) or a heterocyclic group; $R^2$ is a group of the formula:

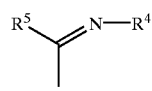

wherein $R^4$ is protected amino or hydroxy, and $R^5$ is hydrogen or lower alkyl; cyano;

a group of the formula: —A—$R^6$, wherein $R^6$ is an acyl group, and A is a lower aliphatic hydrocarbon group which may have one or more suitable substituent(s);

an amidated carboxyl;

an unsaturated heterocyclic group which may have one or more suitable substituent(s);

amino; or a protected amino; and $R^3$ is hydrogen, lower alkyl, lower alkoxy, or halogen.

2. The method of claim 1, wherein said adenosine $A_1$ antagonist is a pyrazolopyridine compound of the formula:

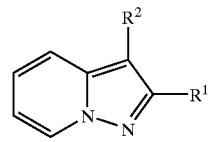

wherein $R^1$ is aryl, and $R^2$ is dihydropyridazinyl having acyl(lower)alkyl and oxo; dihydropyridazinyl having cyclo(lower)alkyl substituted by acyl(lower)alkyl or acyl(lower)alkylidene and oxo; or dihydropyridazinyl having cyclo(lower)alkenyl substituted by acyl(lower)alkyl or acyl(lower)alkylidene and oxo.

3. The method of claim 1, comprising contracting said sperm with the adenosine $A_1$ antagonist 3-[2-(3-carboxypropyl)-3-oxo-2,3-dihydropyridazin-6-yl]-2-phenylpyrazolo[1,5-a]pyridine.

4. The method of claim 1, wherein the adenosine $A_1$ antagonist is a compound having adenosine $A_1$ antagonist activity with an $IC_{50}$ value of not more than 100 μm.

5. The method of claim 1, wherein the adenosine $A_1$ antagonist is a compound having adenosine $A_1$ antagonist activity with an $IC_{50}$ value of not more than 50 μm.

6. The method of claim 1, wherein the adenosine $A_1$ antagonist is a compound having adenosine $A_1$ antagonist activity with an $IC_{50}$ value of not more than 10 μm.

7. The method of claim 1, wherein the adenosine $A_1$ antagonist is a compound having adenosine $A_1$ antagonist activity with an $IC_{50}$ value of not more than 1 μm.

8. The method of claim 1, wherein said adenosine $A_1$ antagonist is administered intraurethrally, intratesticularly, intradeferentially, intrascrotally, or into the female reproductive organ.

9. The method of claim 1, wherein said adenosine $A_1$ antagonist is inistered rectally, orally, parenterally or by inhalation.

10. The method of claim 1 that comprises contacting said sperm with (2R)-1-[3-(2-phenylpyrazolo[1,5-a]pyridin-3-yl)acryloyl]-2-(2-hydroxyethyl)piperidine.

11. The method of claim 1 that comprises contacting said sperm with (2R)-1-[3-(2-phenylpyrazolo[1,5-a]pyridin-3-yl)acryloyl]-2-(carboxymethyl)piperidine.

12. The method of claim 1 that comprises contacting said sperm with 3-[2-(2-carboxymethyl-1-cyclohexenyl)-3-oxo-2,3-dihydropyridazin-6-yl]-2-phenylpyrazolo[1,5-a]pyridine.

13. The method of claim 1 that comprises contacting said sperm with said adenosine $A_1$ antagonist in vitro.

14. The method for treating sperm used in a process of artificial insemination or in vitro fertilization comprising:

contacting ejaculated seminal fluid or purified sperm with an amount of an adenosine $A_1$ antagonist suitable for promoting a sperm acrosomal reaction, and contacting said seminal fluid or purified sperm with an ovum, wherein said adenosine $A_1$ antagonist is a pyrazolopyridine compound of the following general formula or a salt thereof:

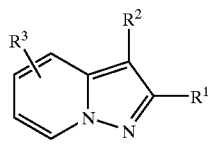

wherein $R^1$ is lower alkyl, aryl which may have one or more suitable substituent(s) or a heterocyclic group;

$R^2$ is a group of the formula:

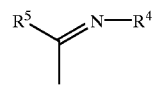

wherein $R^4$ is protected amino or hydroxy, and $R^5$ is hydrogen or lower alkyl; cyano;

a group of the formula: —A—$R^6$, wherein $R^6$ is an acyl group, and A is a lower aliphatic hydrocarbon group which may have one or more suitable substituent(s);

an amidated carboxyl;

an unsaturated heterocyclic group which may have one or more suitable substituent(s);

amino; or a protected amino; and $R^3$ is hydrogen, lower alkyl lower alkoxy, or halogen.

* * * * *